United States Patent [19]

Lauffer et al.

[11] Patent Number: 4,899,755

[45] Date of Patent: Feb. 13, 1990

[54] HEPATOBILIARY NMR CONTRAST AGENTS

[75] Inventors: Randall B. Lauffer, Boston; Thomas J. Brady, Winchester, both of Mass.

[73] Assignee: The General Hospital Corporation, Boston, Mass.

[21] Appl. No.: 731,841

[22] Filed: May 8, 1985

[51] Int. Cl.$^4$ .................. A61K 43/00; A61K 49/02
[52] U.S. Cl. .................................................. 128/654
[58] Field of Search ............... 128/653, 654; 424/4, 424/9; 260/429 J; 600/3-4, 12

[56] References Cited

U.S. PATENT DOCUMENTS

| | | | |
|---|---|---|---|
| 4,150,047 | 4/1979 | Coe et al. | 260/429 J |
| 4,308,249 | 12/1981 | Frank et al. | 424/9 |
| 4,331,647 | 5/1982 | Goldenberg | 424/9 |
| 4,352,751 | 10/1982 | Wieder et al. | 260/429 J |
| 4,361,544 | 11/1982 | Goldenberg | 424/9 |
| 4,401,647 | 8/1983 | Krohn et al. | 128/659 |
| 4,472,509 | 9/1984 | Gansaw et al. | 424/9 |
| 4,615,879 | 10/1986 | Ringe et al. | 424/9 |
| 4,639,365 | 1/1987 | Sherry | 128/653 |
| 4,647,447 | 3/1987 | Gries et al. | 424/9 |

FOREIGN PATENT DOCUMENTS

| | | |
|---|---|---|
| 8633082 | 1/1983 | Australia . |
| 0133603 | 12/1983 | European Pat. Off. ............... 429/9 |
| 2606721 | 9/1976 | Fed. Rep. of Germany . |
| 3129906 | 2/1983 | Fed. Rep. of Germany . |

OTHER PUBLICATIONS

Brasch et al., "Contrast-Enhanced NMR Imaging: Animal Studies Using Gadolinium-DTPA Samples" in *AJR 142*, pp. 625-630, Mar. 1984.

Felix et al., "Brain Tumors NMR Imaging with Gadolinium DTPA" in *Radiology 56*, 681-88 (1985).

Unger et al., "Magnetic Resonance Imaging Using Gd-Labeled Monoclonal Antibody," *Invert. Radiology 20*, (1985) pp. 693-700.

Chen C., Cohen J. S., Myers C. E. and John M., Paramagnetic Metalloporphyrins as Potential Contrast Agents in NMR Imaging in *FEBS Letters*, vol. 168, No. 1, Mar. 1984, pp. 70-74.

Weinman et al., Characteristics of Gadolinium-DTPA Complex, A Potential NMR Contrast Agent in *AJR* Mar. 1984, pp. 619-624.

Haddock et al. Proc. Soc. Exptl. Biol. Med. 120:663 (1965).

Bagley et al. Proc. Soc. Exptl. Biol. Med. 127:798 (1968).

*Primary Examiner*—C. Fred Rosenbaum
*Attorney, Agent, or Firm*—Fish & Richardson

[57] ABSTRACT

A method of altering proton NMR relaxation times in the liver or bile duct of a human patient involving administering to the patient an agent characterized in that it is taken up preferentially by human hepatocytes, compared to human reticuloendothelial cells, and it contains a paramagnetic substance capable of altering the proton NMR relaxation times in the hepatocytes.

24 Claims, No Drawings

HEPATOBILIARY NMR CONTRAST AGENTS

BACKGROUND OF THE INVENTION

This invention relates to diagnostic NMR imaging.

NMR imaging has been used in medical diagnosis for a number of years. The use of contrast agents to enhance its diagnostic utility has only recently appeared. For example, Gries et al. German Patent DE No. 3,129,906 describes NMR contrast agents which consist of a paramagnetic ion complexed with a chelating agent and a base or acid, e.g., the di N methylglucosamine salt of manganese chelated with EDTA.

SUMMARY OF THE INVENTION

The present invention provides a method of imaging the liver and bile duct of a human patient, and visualizing space filling hepatic and bile duct lesions. The method generally involves altering proton NMR relaxation times in the patient by administering an NMR contrast agent characterized in that it is taken up specifically by human hepatocytes, compared to human reticuloendothelial cells, and it contains a paramagnetic substance capable of altering the proton NMR relaxation times in the hepatocytes.

The invention, because it employs agents taken up preferentially by hepatocytes, which make up the bulk of the liver, provides superior NMR imaging of the liver, and allows visualization of hepatocarcinoma or metastatic tumors, whose cells take up the agent at a different rate, or retain the agent for a different length of time, than normally functioning hepatocytes. The invention also allows the use of NMR imaging to monitor liver function, as manifested by uptake or retention rates of the contrast agents of the invention. Agents can be used in which the toxic paramagnetic ion (e.g., gadolinium) is shielded by the steric bulk of a chelating agent, to reduce toxicity; it has been found that such agents are effective in reducing $T_1$ (discussed below), despite the relatively lower accessibility of the paramagnetic ion to the surrounding water protons.

Other features and advantages of the invention will be apparent from the following description of the preferred embodiments thereof, and from the claims.

DESCRIPTION OF THE PREFERRED EMBODIMENTS

Preferred embodiments of the invention are described below.

PROPERTIES OF CONTRAST AGENTS

The preferred NMR contrast agents of the invention possess a number of physical/chemical properties, discussed below, related to their utility in imaging the liver, particularly metastases. In order for the agents to provide the NMR contrast needed for such imaging, they must alter the proton NMR relaxation time in hepatocytes, which make up the bulk of the liver. It is the hepatocytes in which enhanced NMR contrast must be achieved, rather than reticuloendothelial (RE) cells, or water protons in the extracellular space of the liver. Thus the agents must have properties which cause them to be taken up by hepatocytes to a greater extent than by the RE cells of the liver. It is also desired that, at the time the NMR imaging is carried out on the liver of the patient, the contrast agent be present in different concentrations in normally functioning hepatocytes than in liver tumor cells, e.g., hepatocarcinoma cells. This difference is achieved either by means of a different rate of uptake of the contrast agent by normal and cancerous hepatocytes, or by a different retention profile. E.g., the agent has properties which render it taken up to a large degree by normally functioning hepatocytes and to a small degree by cancerous hepatocytes; or which render it retained longer in normal hepatocytes than in cancerous hepatocytes. NMR contrast is achieved by the altering, by the paramagnetic portion of the agent, of $T_1$ (spin-lattice relaxation time) or $T_2$ (spin relaxation time) of the water protons in the hepatocytes.

Molecular Weight

The agents preferably have a molecular weight of at least 250, and more preferably over 300, to maximize hepatocellular uptake.

Solubility

To facilitate administration and uptake, the agents should have good water solubility, and preferably should be soluble to a concentration of at least 1.0 mM in normal saline.

Lipophilicity

Preferred contrast agents are sufficiently lipophilic to be taken up preferentially by normally functioning hepatocytes. Sufficient lipophilicity is provided by a nonpolar structure, the presence of at least one aryl group (e.g., a substituted or unsubstituted phenyl ring), at least one halogen atom, and/or hydrophobic alkyl groups. For lipophilicity, it is also desirable that the contrast agent not carry excessive charge, i.e., of absolute value greater than 2, at physiological pH.

Lipophilicity is expressed in terms of octanol:water coefficient, determined by introducing a small amount ($\sim 0.1$ mM) of the radiolabeled contrast agent into equal volumes of octanol and Tris buffer (50 mM, pH 7.4). The coefficient of the agents of the invention is preferably at least 0.005, and more preferably at least 0.01.

Another index related to lipophilicity is that of protein binding. Binding of a hepatobiliary agent in plasma reduces the rate of concomitant renal excretion and thus allows for greater hepatocellular uptake. Binding capacity can be expressed as the percentage of the agent bound to 4.5% human serum albumin (HSA) at a concentration of 0.2 mM of the agent, as determined by equilibrium dialysis. Preferably at least 15%, and more preferably at least 50%, of the agent, binds to HSA.

Relaxivity

The contrast agents of the invention must, as mentioned above, lower either $T_1$ or $T_2$ in hepatocytes. The ability to achieve this is referred to as "relaxivity."

For complexes in which the paramagnetic ion is other than iron (iron is a special case, discussed below), reactivity is optimal where the paramagnetic ion, when bound to the chelating ligand, still has one or more open coordination sites for water exchange. Generally, one or two such sites are preferred, since the presence of more than two open sites in general will unacceptably increase toxicity by release of the metal ion in vivo.

In vitro relaxivity is expressed in units of $s^{-1} mM^{-1}$, or change in $1/T_1$ or $1/T_2$ per mM agent, as measured in saline at 20 MHz. Preferably the agents have an in vitro relaxivity of at least $0.5\ s^{-1}\ mM^{-1}$, more preferably at least $1.0\ s^{-1}\ mM^{-1}$.

Relaxivity can also be measured in vivo for the tissue of interest. In vivo relaxivity is expressed in units of $s^{-1}$ ($\mu$mol/gram of tissue)$^{-1}$, representing the change in $1/T_1$ or $1/T_2$ above that of saline injected controls caused by the agents, divided by the concentration of the agent (in $\mu$mol/gram of tissue). Tissue concentration is measured using agents made with radiolabeled paramagnetic ions. Preferably, the in vivo relaxivity of the agents in liver tissue is at least $1.0 \, s^{-1} (\mu mol/g)^{-1}$.

Relaxivity (and perhaps uptake as well) can also be increased by providing a high degree of binding of the contrast agents to hepatic intracellular proteins like ligandin. The immobilization of paramagnetic agents increases their relaxivity five to ten fold by altering the effective correlation time of the electron nuclear interaction, as described in Lauffer et al. (1985) Magn. Res. Imaging 3, 11. This increased relaxivity will allow for lower doses of the contrast agents and thus a higher margin of safety in their use. Increased binding to liqandin and other intracellular proteins can be achieved by increasing the lipophilicity of the agents as described previously.

A different strategy to increase the relaxivity of metal complexes is to alter the configuration of the donor atoms around the metal ions to achieve the most symmetrical orientation. This symmetry of the ligand field will lead to longer electron spin relaxation times, and higher relaxivities. The DOTA ligands for $Gd^{+3}$. (described below) are an example in which the symmetry is very high (almost cubic) compared to, e.g., DTPA derived liqands (described below), which wrap around the metal ion in an anisotropic fashion. An additional benefit of symmetry constrained macrocyclic liqands like DOTA is their high kinetic stability (vide infra).

Toxicity

The contrast agents must have acceptably low toxicity levels at the dosage required for contrast enhancement, and preferably have an $LD_{50}$ of at least 0.05 mmol/kg. Toxicity of the contrast agents is a function of both the inherent toxicity of the paramagnetic portion of the complex, and of the degree to which the paramagnetic substance dissociates from the chelating agent; toxicity generally increases with the degree of dissociation. For complexes in which kinetic stability is low, a high thermodynamic stability (a formation constant of at least $10^{15} \, M^{-1}$, and more preferably at least $10^{25} \, M^{-1}$) is desirable to minimize dissociation and its attendant toxicity. For complexes in which kinetic stability is comparatively higher, dissociation can be minimized with a lower formation constant, i.e., $10^{10} M^{-1}$ or higher. Kinetically stable complexes generally contain a paramagnetic metal ion, e.g., gadolinium (III), complexed with a highly constrictive chelating agent, e.g., dibenzo-1, 4, 7, 10-tetraazacyclotetradecene 1, 4, 7, 10-tetraacetic acid (dibenzo DOTA).

Toxicity is also a function of the number of open coordination sites in the complex; the fewer open coordination sites, the less tendency there is, generally, for the chelating agent to release the cytotoxic paramagnetic ion. Preferably, therefore, the complex contains two, one or zero open coordination sites. The presence of one or even two open coordination sites can be acceptable in agents in which the paramagnetic substance has a high magnetic moment (i.e., is strongly paramagnetic), and can thus affect $T_1$ or $T_2$ at a low dosage; an example is gadolinium, which is strongly paramagnetic owing to its seven unpaired electrons. In the case of iron, there should be no open coordination sites; i.e., the chelating ligand should completely enclose the iron ion, to prevent the formation of the cytotoxic hydroxyl radical, which can be generated by the Fenton reaction in the presence of superoxide and iron complexes with open coordination sites (see Grof et al. (1984) J. Biol Chem. 259, 3620).

Paramagnetic Substance

The paramagnetic portion of the contrast agents of the invention can be any paramagnetic ion of the transition metal or lanthanide series which has at least one, and more preferably five or more, unpaired electrons, and a magnetic moment of at least 1.7 Bohr magneton. Suitable ions include gadolinium (III), iron (III), manganese (II and III), chromium (III), copper (II), dysprosium (III), terbium (III), holmium (III), erbium (III), and europium (III); most preferred are gadolinium (III), and iron (III), and manganese (II).

Chelating Ligand

The organic chelating ligand should be physiologically compatible and should contain at least 1 aryl ring which may be substituted with halogen atoms and/or $C_1$-$C_{10}$ alkyl groups. The molecular size of the chelating ligand should be compatible with the size of the paramagnetic substance. Thus gadolinium (III), which has a crystal ionic radius of 0.938A, requires a larger chelating ligand than iron (III), which has a crystal ionic radius of 0.64A.

One suitable class of chelating liqands are ethylene-bis-(2-hydroxyphenylglycine) ("EHPG"), and derivatives thereof, including 5-Cl-EHPG; 5Br-EHPG; 5-Me-EHPG; 5t-Bu-EHPG; and 5sec-Bu-EHPG. EHPG and derivatives thereof have the structure:

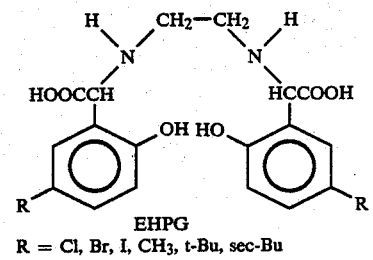

EHPG

R = Cl, Br, I, $CH_3$, t-Bu, sec-Bu

Although substitution at the 5 position of EHPG is the most effective in increasing lipophilicity, substitution at any position on the two phenyl rings can be used.

Another suitable class of chelating liqands are benzodiethylenetriamine pentaacetic acid (benzo-DTPA) and derivatives thereof, including dibenzo-DTPA; phenyl-DTPA; diphenyl-DTPA; benzyl-DTPA; and dibenzyl DTPA. Two of these compounds have the structures shown below:

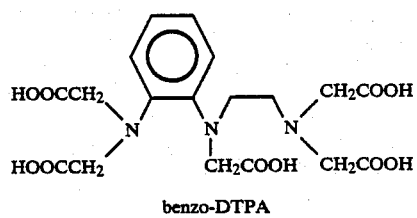

benzo-DTPA

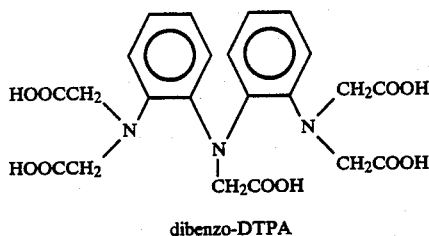

dibenzo-DTPA

Another class of suitable chelating ligands are bis-2 (hydroxybenzyl)-ethylene-diaminediacetic acid (HBED) and derivatives thereof. The structure of HBED is shown below:

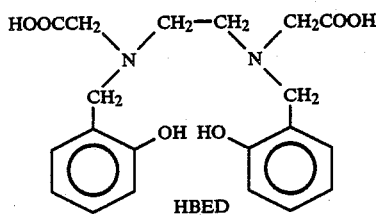

HBED

The HBED ligand advantageously has a very high formation constant for iron of $10^{40}$. This ligand is available from the Strem Chemical Company.

Another suitable class of chelating ligands is the class of macrocyclic compounds which contain at least 3 carbon atoms, more preferably at least 6, and at least two hetero (O and/or N) atoms. The macrocyclic compounds can consist of one ring, or two or three rings joined together at the hetero ring elements. One suitable class of mono-macrocyclic chelating ligands has the general formula

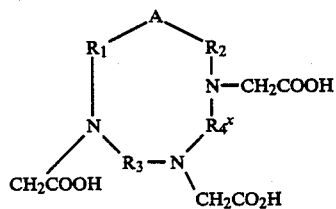

where A is

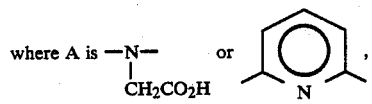

X is 0 or 1, and each $R_1$, $R_2$, $R_3$, and $R_4$, independently, is ethyl, propyl, or

, provided that when A is

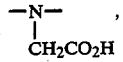

at least one group must be

.

The aryl groups may be substituted with halogen atoms or $C_1$–$C_4$ alkyl groups. Examples of suitable macrocyclic ligands include benzo-DOTA, where DOTA is 1, 4, 7, 10-tetraazacyclotetradecane-1, 4, 7, 10-tetraacetic acid; dibenzo-DOTA; and benzo-NOTA, where NOTA is 1, 4, 7-triazacyclononane N, N', N"-triacetic acid.

Synthesis

The contrast agents of the invention can be synthesized from commercially available or readily synthesized reagents using conventional synthetic methods. In general, a salt of the paramagnetic ion is added to a slightly alkaline (pH 7.4–9) aqueous solution of the chelating ligand and the resulting mixture is stirred for 3–24 hours at room temperature. The resulting contrast agent is then used immediately or stored in lyophilized form or in physiological buffer until use.

The synthesis of iron (III)-(EHPG)$^-$ is carried out as follows. EHPG (Sigma) is dissolved at room temperature in distilled, deionized water maintained at pH 8–9 by addition of 1M NaOH. Solid $FeCl_3$—$6H_2O$ is added to the solution and the pH adjusted to 7.4 with 1M NaOH. The resulting dark red solution is then stirred at room temperature for 30 minutes, after which it is filtered with 0.2 $\mu m$ micropore filters (Gelman). The concentration of iron (III)-(EHPG)$^-$ is determined by visible absorption of diluted aliquots using a Beckman Spectrophotometer and an extinction coefficient at 480 nm of 4300 $CM^{-1}M^{-1}$.

To make iron chelates of EHPG derivatives the first step is to make the appropriate EHPG derivative, according to Mannich reaction, described in Theodorakis et al. (1980) J. Pharm. Sci 69, 581; the reaction employs ethylenediamine, dichloroacetic acid, and the appropriate parasubstituted phenol. The reaction scheme for 5-Br-EHPG is:

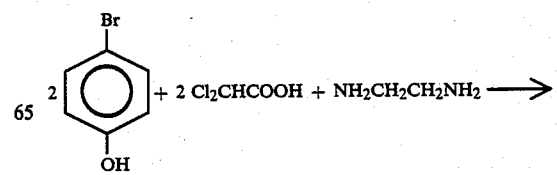

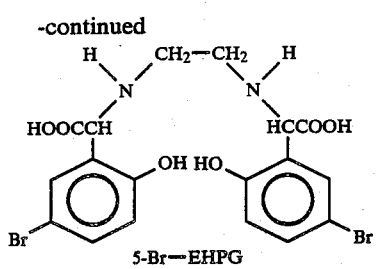

5-Br—EHPG

Iron (III)-(5-Cl-EHPG)⁻, iron (III)-(5-Bu-EHPG)⁻, iron (III)-(5-Me-EHPG)⁻, and iron (III)-HBED are prepared in analogous fashion to iron-EHPG.

The structure of iron-EHPG is:

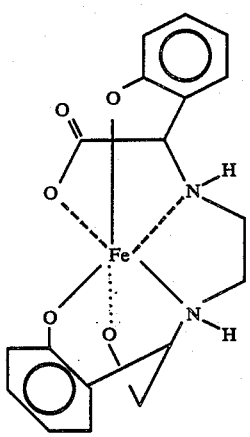

The octanol/water partition coefficients and HSA binding percentages of Iron-EHPG, Iron-(5-Br-EHPG), and Iron (HBED) are shown below:

|  | $\frac{[\text{octanol}]}{[\text{water}]}$ | % bound to HSA |
|---|---|---|
| Iron-EHPG | 0.013 | 17 |
| Iron-(5-Br—EHPG) | 0.89 | 82 |
| Iron-HBED | 0.050 | 34 |

The macrocyclic DOTA chelating ligands are synthesized generally as described in Desreux et al. (1980) Inorg. Chem. 19, 1319, generally according to the reaction

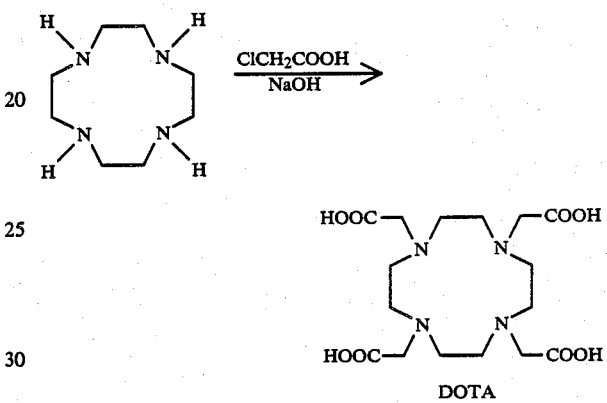

DOTA itself lacks sufficient lipophilic groups for hepatocellular uptake. Two derivatives with the required lipophilicity (provided by fused phenyl rings), benzo-DOTA and dibenzo-DOTA, are made according to the general reaction scheme:

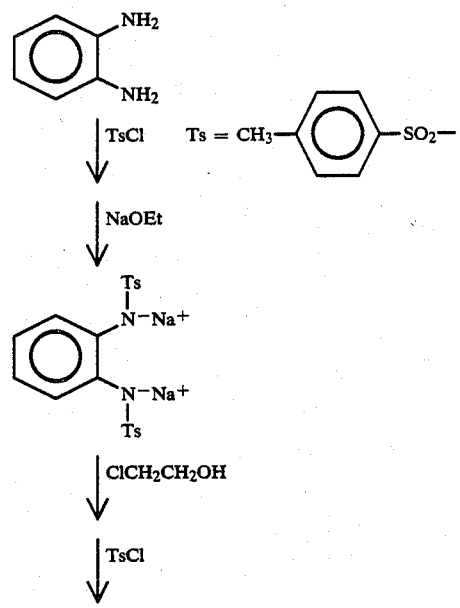

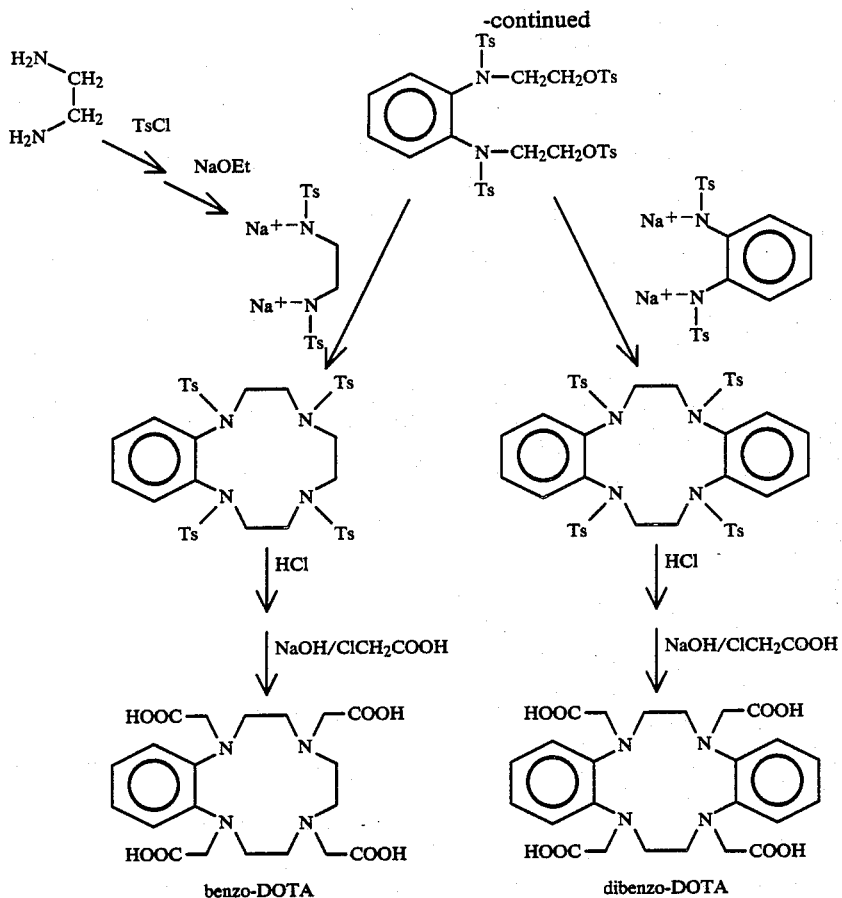

DTPA derivatives (e.g., benzo-DTPA and dibenzo-DTPA) are made by methods analogous to the methods used for making benzo-EDTA (McCandlish et al. (1978) Inorg. Chem. 17, 1383).

Paramagnetic ion chelating ligand complexes made using DOTA derivatives are made generally as described earlier, with a longer time (24 hours) and higher reaction temperatures being required for the formation of metal ion/macrocyclic ligand complexes.

Use

The contrast agents of the invention are administered orally or intravenously in physiological buffer. Dosage depends on the sensitivity of the NMR imaging instrumentation, as well as on the composition of the contrast agent. For example, a contrast agent containing a highly paramagnetic substance, e.g., gadolinium (III), generally requires a lower dosage than a contrast agent containing a paramagnetic substance with a lower magnetic moment, e.g., iron (III). In general, dosage will be in the range of about 0.001–1 mmol/kg, more preferably about 0.01–0.1 mmol/kg.

Following administration of the contrast agent, conventional NMR imaging is carried out; the choice of pulse sequence (inversion recovery, IR; spin echo, SE) and the values of the imaging parameters (echo time, TE; inversion time, TI; repetition time, TR) will be governed by the diagnostic information sought. In general, if one desires to measure $T_1$, then TE should be less than 20 milliseconds to minimize competing $T_2$ effects. Conversely, if one desires to measure $T_2$, then TE should be greater than 20 milliseconds to minimize competing $T_1$ effects. TI and TR will remain approximately the same for both $T_1$- and $T_2$-weighted images; TI and TR are generally on the order of about 200–600 and 100–1000 milliseconds, respectively.

NMR Imaging Using Iron (III)-(EHPG)

Iron (III)-(EHPG)$^-$ was prepared as described above and used for in vivo imaging of rat livers as follows.

Fasted male Sprague Dawley rats (of average weight of about 400 g) were anesthetized with intraperitoneal pentobarbitol (50 mg/kg), placed on a calibrated carrier, and subjected to NMR imaging, along with calibration tubes containing paramagnetically-doped water or agar gels of known $T_1$ and $T_2$, to establish an initial baseline image. NMR imaging was performed with a horizontal bore (8 cm) superconducting with a horizontal bore (8 cm) superconducting magnet system (Technicare Corp.) at a magnetic field strength of 1.4 tesla ($^1$H resonance of 61.4 MHz). Images were obtained using a 2-D Fourier transform technique with a slice selection determined by selective irradiation. All images were obtained using 128 phase encoded gradient steps. To maximize $T_1$ contrast, an IR pulse sequence was used (TE 15 msec, TI 400 msec, TR 1000 msec).

After baseline images were obtained, the rats were removed from the magnet and injected in the tail vein with 0.2 mmol/kg of iron (III)-(EHPG)$^-$. As a comparison, some rats received 0.2 mmol/kg of iron (III)-(DTPA)$^{-2}$ instead. The rats were then reinserted into the magnet, along with the calibration tubes, in the same position as for the initial baseline imaging. Imaging began immediately and continued for 1.5–3 hours.

Background subtracted, region of interest intensity values of liver and muscle were obtained for each image; these values were then normalized for any alteration in the signal intensity of the calibration tubes.

The IR 1000/400/15 images of rats which received iron (III)-(EHPG)$^-$ demonstrated a marked and prolonged increase in signal intensity of the liver consistent with a short $T_1$. In contrast, images of rats which received iron (III)-(DTPA)$^{-2}$, demonstrated only small and transient increases in liver intensity. This is presumably because, unlike iron (III)-(EHPG)$^-$, iron (III)-(DTPA)$^{-2}$ distributes throughout the extracellular liver space, rather than in functioning hepatocytes, and is rapidly excreted into the urine.

Ex vivo biodistribution studies measuring the $T_1$ and $T_2$ values of excised rat liver, blood, spleen, and thigh muscle at various post injection times also demonstrated that iron (III)-(EHPG)$^-$ is predominantly taken up by functioning hepatocytes, and thus decreases the relaxation times of water protons in these cells.

Rats given intravenous doses of 2.0 mmol/kg of iron EHPG suffered no apparent ill effects over a two-week observation period.

It is believed that the mechanism of operation of iron-EHPG is as follows. Relaxation time enhancement normally occurs where the unpaired electrons of the paramagnetic substance interact with water molecules directly bound to the paramagnetic substance; the degree of enhancement is inversely related to the distance from the paramagnetic center to the water molecules. In iron (III)-(EHPG)-, however, there are no directly bound water molecules. Relaxation time enhancement, therefore, probably results mainly from the interaction between the paramagnetic substance and indirectly bound, outer-sphere water molecules. It is believed that since there is a sufficiently large number of these outer-sphere water molecules, appreciable relaxation time enhancement occurs despite the large distance between the water molecules and the paramagnetic substance.

Other embodiments are within the following claims.

We claim:

1. A method of altering proton NMR relaxation times in the liver or bile duct of a human patient comprising administering to said patient an agent characterized in that
   it is taken up preferentially by human hepatocytes, compared to human reticuloendothelial cells,
   it contains a complex of a paramagnetic substance capable of altering said proton NMR relaxation times in said hepatocytes,
   and an organic chelating ligand, said complex having a formation constant of at least $10^{15} M^1$, a solubility to at least 1.0 mM concentration in normal saline, a molecular weight greater than 250, and a charge of an absolute value of 2 or less,
   said organic chelating ligand containing at least one aryl ring, and
   said paramagnetic substance being selected from the group consisting of gadolinium (III), iron (III), manganese (II), manganese (III), chromium (III), copper (II), dysprosium (III), terbium (III), holmium (III), erbium (III) and europium (III).

2. The method of claim 1, further comprising, following said administration of said agent, subjecting said patient to NMR imaging.

3. The method of claim 1 wherein said paramagnetic substance is further characterized in that
   it contains at least 1 unpaired electron and
   it has a magnetic moment of at least 1.7 Bohr magneton.

4. The method of claim 3 wherein said paramagnetic substance contains at least 5 unpaired electrons.

5. The method of claim 4 wherein said paramagnetic substance contains 7 unpaired electrons.

6. The method of claim 1 wherein said complex is further characterized in that its lipophilicity is sufficiently high to cause it to be taken up in greater amount by normally functioning human hepatocytes than by hepatocarcinoma cells.

7. The method of claim 1 wherein said complex contains at least one halogen atom.

8. The method of claim 1 wherein said complex has an $LD_{50}$ of at least 0.05 mmol/kg.

9. The method of claim 1 wherein said complex contains zero open sites for water coordination.

10. The method of claim 1 wherein said complex contain one or more open sites for water coordination.

11. The method of claim 1 wherein said agent is further characterized in that it exhibits an octanol:water coefficient of at least 0.005.

12. The method of claim 11 wherein said agent is further characterized in that it exhibits an octanol:water coefficient of at least 0.01.

13. The method of claim 1 wherein said agent is further characterized in that at least 15% of said agent binds to 4.5% human serum albumin at a concentration of 0.2 mM agent.

14. The method of claim 13 wherein at least 50% of said agent binds to 4.5% human serum albumin at a concentration of 0.2 mM agent.

15. The method of claim 1 wherein the in vitro relaxivity in saline of said agent at 20 MHz is at least $5\ s^{-1}\ mM^{-1}$.

16. The method of claim 15 wherein said in vitro relaxivity is at least $1.0\ s^{-1}\ mM^{-1}$.

17. The method of claim 1 wherein the in vivo relaxivity in liver tissue of said agent is at least $1.0\ s^{-1}\ (\mu mol/g)^{-1}$.

18. The method of claim 1 wherein said organic chelating ligand is a macrocyclic compound containing at least 3 carbon atoms and at least two hetero atoms.

19. The method of claim 18 wherein said macrocyclic compound has the formula

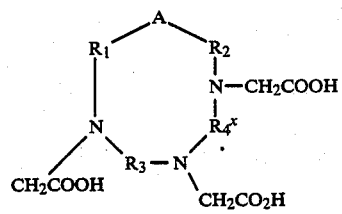

where A is

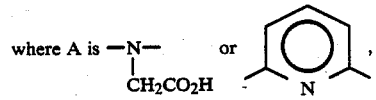

X is 0 or 1, and each $R_1$, $R_2$, $R_3$ and $R_4$, independently, is ethyl, propyl, or provided that when A is

$$-\underset{\underset{CH_2CO_2H}{|}}{N}-,$$

at least one group must be

20. The method of claim 19 wherein said macrocyclic compound is a derivative of 1,4,7,10-tetraazacyclotetradecane-1,4,7,10-tetraacetic acid which contains at least one aryl ring.

21. The method of claim 1 wherein said organic chelating ligand is benzodiethylenetriamine or a derivative thereof.

22. The method of claim 1 wherein said organic chelating ligand is bis-2 (hydroxybenzyl)-ethylenediamineacetic acid or a derivative thereof.

23. The method of claim 1 wherein said organic chelating ligand is ethylenebis-(2-hydroxyphenylglycine) or a derivative thereof.

24. The method of claim 23 wherein said derivative is substituted at the 5-position on its phenyl rings with Cl, Br, Me, t-Bu, or sec-Bu.

* * * * *

UNITED STATES PATENT AND TRADEMARK OFFICE
CERTIFICATE OF CORRECTION

PATENT NO. : 4,899,755
DATED : February 13, 1990
INVENTOR(S) : Randall B. Lauffer et al.

It is certified that error appears in the above-identified patent and that said Letters Patent is hereby corrected as shown below:

On the face of the patent, under "OTHER PUBLICATIONS" add "Theodrakis et al. (1980) J. Pharm. Sci. 69, 581";

On the face of the patent, under "OTHER PUBLICATIONS", add "Desreux et al. (1980) Inorg. Chem. 19, 1319";

Col. 2, line 57, "reactivity" should be --relaxivity--;

Col. 12, claim 15, line 36, "5 $s^{-1}$ $mM^{-1}$" should be --0.5 $s^{-1}$ $mM^{-1}$--.

Signed and Sealed this

First Day of October, 1991

Attest:

Attesting Officer

HARRY F. MANBECK, JR.

Commissioner of Patents and Trademarks

UNITED STATES PATENT AND TRADEMARK OFFICE
CERTIFICATE OF CORRECTION

PATENT NO.   : 4,899,755
DATED        : February 13, 1990
INVENTOR(S)  : RANDALL B. LAUFFER ET AL.

It is certified that error appears in the above-identified patent and that said Letters Patent is hereby corrected as shown below:

Column 1, line 1, please add the following:

--This invention was made with government support under CA07671 and CA42430 awarded by the National Cancer Institute of the National Institutes of Health. The government has certain rights in the invention.--

Signed and Sealed this

Fifteenth Day of September, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO.        : 4,899,755
APPLICATION NO. : 06/731841
DATED             : February 13, 1990
INVENTOR(S)       : Lauffer et al.

Page 1 of 1

It is certified that error appears in the above-identified patent and that said Letters Patent is hereby corrected as shown below:

Please add the following new paragraph at column 1, line 3.

--<u>GOVERNMENT FUNDING</u>

This invention was made with Government support under Grant Nos. CA042430 and CA007671 awarded by the National Institutes of Health. The Government has certain rights in this invention.--

Signed and Sealed this

Eighteenth Day of August, 2009

David J. Kappos
*Director of the United States Patent and Trademark Office*